United States Patent
Mattanovich et al.

(10) Patent No.: US 7,351,549 B2
(45) Date of Patent: Apr. 1, 2008

(54) METHOD FOR THE MANUFACTURE OF RECOMBINANT TRYPSIN

(75) Inventors: Diethard Mattanovich, Vienna (AT);
Hermann Katinger, Vienna (AT);
Hubertus Hohenblum, Vienna (AT);
Stefan Naschberger, Vienna (AT);
Robert Weik, Vienna (AT)

(73) Assignee: Polymun Scientific Immunbiologische Forschung GmbH, Vienna (AT)

( * ) Notice: Subject to any disclaimer, the term of this patent is extended or adjusted under 35 U.S.C. 154(b) by 494 days.

(21) Appl. No.: 10/181,808

(22) PCT Filed: Jan. 24, 2001

(86) PCT No.: PCT/EP01/00770
§ 371 (c)(1),
(2), (4) Date: Dec. 16, 2002

(87) PCT Pub. No.: WO01/55429
PCT Pub. Date: Aug. 2, 2001

(65) Prior Publication Data
US 2003/0157634 A1   Aug. 21, 2003

Related U.S. Application Data

(60) Provisional application No. 60/177,348, filed on Jan. 24, 2000.

(51) Int. Cl.
*C12N 15/00* (2006.01)
*C12Q 1/68* (2006.01)
*C12P 21/04* (2006.01)
*C12N 15/63* (2006.01)

(52) U.S. Cl. .................. 435/69.1; 435/6; 435/69.7; 435/69.9

(58) Field of Classification Search .............. None
See application file for complete search history.

(56) References Cited

U.S. PATENT DOCUMENTS 5,521,086 A * 5/1996 Scott et al. ............. 435/254.2

FOREIGN PATENT DOCUMENTS

| WO | WO 97/00316 | * | 1/1997 |
| WO | WO 99/18219 | * | 4/1999 |

OTHER PUBLICATIONS

Emi, M. et al, Cloning, characterization and nucleotide sequences of two cDNAs encoding human pancreatic trypsinogen. Gene 41: 305-310 (1986).*
Bouffard, G.G. et al. A Collection of 1814 Human Chromosome 7-Specific STSs. Genome Research 7: 59-64 (1997).*
Brodrick, J.W. et al. Human Cationic Trypsinogen: Purification, Characterization, and Characteristics of Autoactivation. The Journal of Biological Chemistry 253(8): 2732-2736 (1978).*
Kay, J., et al., "The Autoactivation of Trypsinogen", The Journal of Biological Chemistry, vol. 246, No. 21, 1971, pp. 6661-6665, XP-001030933.
Sahin-Toth, M., et al., "High-Affinity $CA^{2+}$ Binding Inhibits Autoactivation of Rat Trypsinogen", Biochemical and Biophysical Research Communications, vol. 275, No. 2, Aug. 28, 2000, pp. 668-671, XP-002181528.

* cited by examiner

*Primary Examiner*—David Guzo
*Assistant Examiner*—Michele K. Joike
(74) *Attorney, Agent, or Firm*—Rothwell Figg Ernst & Manbeck P.C.

(57) ABSTRACT

The present invention relates to a method for the manufacture and purification of recombinant trypsinogen and trypsin in *E. coli* and yeast, using high yield expression vectors with and without secretion leader sequences. The invention further relates to an improved method and apparatus for carrying out protein refolding specifically useful for processing trypsinogen that has accumulated intracellularly in the form of inclusion bodies.

22 Claims, 1 Drawing Sheet

METHOD FOR THE MANUFACTURE OF RECOMBINANT TRYPSIN

The present application is a 371 of PCT/EP01/00770 filed on Jan. 24, 2001 which claims the benefit of 60/177,348 filed on Jan. 24, 2000.

TECHNICAL FIELD

The present invention is in the field of molecular biology and biotechnology and relates to methods for the manufacture of recombinant trypsinogen and trypsin, respectively.

BACKGROUND OF THE INVENTION

The protease trypsin is used in biotechnology for different purposes, e.g. to detach adherent cells from surfaces, to enhance viral infection during virus production, or to process fusion proteins. Today, trypsin prepared from animal, particularly bovine and porcine tissue is still in widespread use. As it is a general desire and tendency to replace material, e.g., proteins, extracted from animal sources by equivalents made by recombinant technology it is an objective of the present invention to provide for a method to efficiently produce recombinant trypsin of high purity and in high amounts.

As is known in the art, the proteolytic activity of trypsin poses two major obstacles for recombinant production thereof:

Trypsin activity seriously damages the host cell. Therefore the direct production of active trypsin yields very low expression levels (Yee L. and Blanch H. W., 1992, Biotechnol. Bioeng. 41, 781-790). To circumvent this problem, the inactive precursor trypsinogen may be expressed instead of the mature trypsin.

Trypsinogen is, however, susceptible to digestion by trypsin and other proteases (Abita J. P. et al. 1969, European J. Biochem. 8, 314-324) resulting in its cleavage to active trypsin. It is further known in the art that trypsin may act on itself and autocatalyze its own cleavage to finally become inactivated.

In this context, WO97/00316 reports that the recombinant production of trypsinogen by a filamentous fungus even when secreted into the medium by the host cell will yield at least some mature trypsin due to either automaturation or maturation by proteases produced by the host cell.

EP 597681 reports methods for the construction of suitable vectors for recombinant production of trypsin or trypsinogen in an *E.coli* expression system. They also teach that conversion of trypsinogen to trypsin is accomplished by enteropeptidase.

EP 597681 is silent with regard to culturing the successfully transformed *E.coli* cells on another than a solid agar medium and thus do not indicate any advantages or disadvantages of this procaryotic expression system. On the other hand, the methods disclosed in WO97/00316 allegedly yield a several fold increased trypsin level as compared to those apparent from other microbial systems, without providing any basis for such a comparison, however. WO97/00316 also teaches that the expression of trypsins, especially mammalian trypsins, is accomplished to only extremely low levels in the art.

The presence of two protein species (e.g., trypsinogen and trypsin) in a bacterial or eukaryotic cell culture broth will likely lead to complications during product recovery and purification, because both proteins need to be harvested and purified. Moreover, in case of microbial trypsinogen secretion the simultaneous presence of trypsin will accelerate the maturation of trypsinogen to trypsin and, subsequently, may lead to at least a partial inactivation of the desired final product trypsin. Even worse, it may additionally damage the host cells resulting in a reduction of the biomass and product yield and to a higher load of undesired contamination by host cell constituents.

WO 00/17332 reports a method for the production of trypsinogen using a modified trypsinogen anlog that cannot be autocatalytically cleaved during incubation. The method requires the addition of a diaminopeptidase for activation of trypsinogen to trypsin after separation of the trypsin analog from the cell culture medium.

On the other hand, WO 99/10503 reports a method for the production of trypsinogen, wherein a synthetic autocatalytic cleavage site is introduced to the trypsinogen molecule that does not occur naturally and which replaces the naturally occurring autocleavage site. It is explicitly desired therein that the zymogen, i.e., the trypsinogen, is autocatalytically active, at least to a low degree. The host cells producing the zymogen are not harmed by the proteolytic activitiy of the zymogen, because the zymogen is accumulated intracellulary in the form of inactive protein aggregates, i.e. inclusion bodies.

All of the aforementioned methods have in common that they require either a step of modifying the trypsinogen molecule in order to increase its autocatalytic activity or, on the contrary, to prevent undesired impact on the producing cells, or require a step of adding a proteinase for activating the zymogen, e.g., trypsinogen trypsinogen to the active enzyme, e.g., trypsin, which then of course further requires removing the proteinase from the final product unless the added proteinase is trypsin.

Therefore it is an objective of the present invention to provide a simple yet highly efficient method suitable for the production of trypsin by recombinant technology without the drawbacks known from the prior art processes.

BRIEF DESCRIPTION OF THE INVENTION

The objective is reached according to the present invention by a method of manufacturing recombinant trypsin or trypsinogen, respectively, during which no unintended trypsin activity nor activation of trypsinogen to trypsin occurs.

In one embodiment, a trypsinogen gene (e.g. human trypsinogen 1) is inserted into yeast expression vectors in a way such that a sequence encoding a secretion leader peptide is included (e.g. pPICZαB for the yeast *Pichia pastoris*), and the recombinant vectors are introduced into appropriate host cells. The cells are cultivated for expression and the recombinant trypsinogen can then be found in the supernatant of the culture, from where it is isolated, purified and activated to trypsin. This procedure was found to be superior to all other expression systems for trypsinogen tested or known to us so far, as it revealed the following important advantages:

the expression level was high;
the trypsinogen protein secreted into the nutrient medium was correctly folded and could be directly activated to trypsin;
no unintended activation to trypsin occurred during the production process.

In another embodiment, a trypsinogen gene is inserted into an expression vector without a secretion leader sequence; so that the product is accumulated inside the host cell, such as a bacterial cell. The trypsinogen forms insoluble aggregates that can be released by breaking up the cells, and harvested by centrifugation, filtration or other methods. To solubilize the recombinant protein, a suitable procedure for denaturing and refolding is applied, preferably by a continuous method as described hereinbelow.

Further embodiments of the present invention are described in the dependent claims.

DETAILED DESCRIPTION OF THE INVENTION

Figure 1:
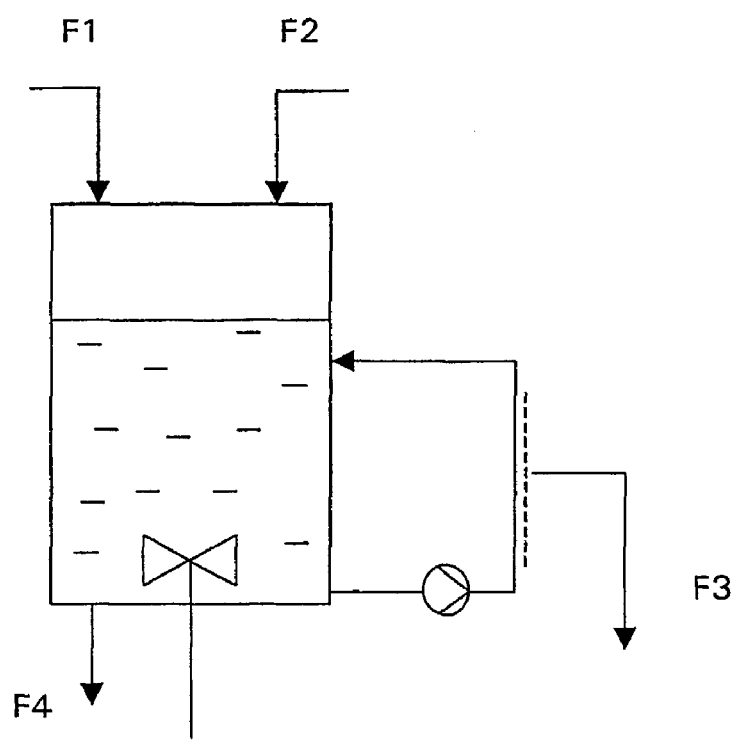
FIG. 1 shows a schematic setup of the refolding device or arrangement as described herein.

The present invention relates to production systems for recombinant trypsin or trypsinogen.

In one embodiment a gene for trypsinogen is introduced into yeast so that the gene product is secreted into the culture supernatant. The yeast can be a methylotrophic yeast (e.g. *Pichia pastoris, P. methanolica* or *Hansenula polymorpha*), or *Saccharomyces cerevisiae, Kluyveromyces lactis* or another yeast. The expression system comprises a promoter (e.g. alcohol oxidase, alcohol dehydrogenase, glyceraldehyde-3-phosphate dehydrogenase or others), a secretion leader (e.g. yeast α-factor, yeast phosphatase, from mammalian or plant source, from trypsinogen, or others), a transcription terminator (e.g. alcohol oxidase, alcohol dehydrogenase or others), and a selective marker (e.g. an amino acid synthesis gene or an antibiotic resistance gene). The recombinant gene and one or more of the additional elements described above are introduced into the yeast cell by e.g. electroporation, treatment with lithium acetate or lithium chloride, preparation of spheroplasts and treatment with calcium salts, or other suitable methods. The yeasts are then cultivated under conditions appropriate for the expression of trypsinogen, and the product is harvested with the culture supernatant.

The product can be further purified from the culture supernatant with a strong cation exchange resin. In most procedures known in the art, the culture supernatant is being exchanged and turned into a buffer having a low conductivity by, e.g., cross flow filtration, dialysis, etc. prior to being loaded onto a gel chromatography column. However, when the culture supernatant is converted to a sodium acetate/acetic acid buffer, only small amounts of trypsinogen contained therein adhere and bind to the cation exchange resin. Therefore a new method is proposed herein, which comprises adding $Ca^{2+}$ ions to the solution that contains the desired product (e.g., trypsinogen, modified trypsinogen, or trypsinogen-homologue) before it is supplied to the gel chromatography column. This can be accomplished by the addition of a soluble calcium salt such as, for example, $CaCl_2$ to said solution at an effective concentration of about 0.5-400, preferably 1-300, most preferably about 5-20 mmol per 1 liter (1 mM). Using this procedure, the trypsinogen-binding capacity of the resin can be augmented by a factor of at least 3, typically by a factor of 3 to 6. The lower limit of $Ca^{2+}$ concentration in the feed solution is primarily determined by the ability of trypsinogen to get activated to trypsin, which ability fades away if the feed solution falls short of $Ca^{2+}$. Under the preferred procedural conditions of the present invention (see Example 5) the minimum $Ca^{2+}$ concentration in the feed solution and preferably also in the washing and eluting buffers has been found to be approximately 1 mM.

The upper limit is basically determined by the degree of conductivity in the feed solution. It was found that in case the conductivity exceeds a certain level (due to the addition of calcium salt), the benefit of increased affinity of ($Ca^{2+}$)-loaded trypsinogen for binding to the chromatography resin gradually fades away. Under the preferred procedural conditions of the present invention (see Example 5) the maximum $Ca^{2+}$ concentration should not exceed 300 mM. For most applications, a $CaCl_2$ concentration of 5 to 20 mM will be best.

Thus the present purification method improves the overall economy and cost-effectiveness of known state-of-the-art purification processes due to an at least threefold increase in binding capacity of the column (which means that at least thrice the usual amount of trypsinogen is bound per volume of resin) and, additionally, due to a significant augmentation of recovery of activatable trypsinogen.

The best results according to the present invention were obtained in a procedure, wherein the harvested culture supernatant, after removal of solids and after addition of an effective amount of $CaCl_2$, was directly, i.e. without a buffer exchanging step, loaded onto the column, and wherein each washing and eluting buffer contained an effective amount of $CaCl_2$. While $Ca^{2+}$ in the feed solution improves binding to the cation exchange resin, $Ca^{2+}$ in the washing and eluting buffers facilitates subsequent activation of trypsinogen to trypsin.

The methods for production of trypsin or trypsinogen that have been described in the art so far either yield very low amounts of the product or cause at least partial cleavage of trypsinogen during the cultivation. This is not the case, however, with the yeast method described herein, which makes this method superior to the hitherto known processes of trypsin production.

In another embodiment of the present invention a gene for trypsinogen is introduced into cells in a way such that the gene product remains in the cytoplasm. The cells can be bacteria (e.g. *Escherichia coli*), yeasts (e.g. *P. pastoris, S. cerevisiae* or others), or any other recombinant host cell. The expression system comprises a promoter (e.g. lac, tac, trc, phage T7 φ10, phage λ $P_L$ or $P_R$, alcohol oxidase, alcohol dehydrogenase, glyceraldehyde-3-phosphate dehydrogenase, or others), a transcription terminator (e.g. rrnB, alcohol oxidase, alcohol dehydrogenase, or others), and a selective marker (e.g. an amino acid synthesis gene or an antibiotic resistance gene).

The recombinant gene together with at least some of the additional elements described above are introduced into the cell by e.g. electroporation, treatment with lithium acetate or lithium chloride, preparation of spheroplasts and treatment with calcium salts, or other suitable methods. The cells are then cultivated under conditions appropriate for the expression of trypsinogen. Then the cells are harvested e.g. by centrifugation and disintegrated mechanically (e.g. pressure, ultrasound) or chemically (e.g. cell wall degrading enzymes, detergents or others). The aggregated trypsinogen accumulated inside the cells in the form of inactive inclusion bodies can be partially purified by washing and subsequently subjected to solubilization by treatment with a chaotropic agent (e.g. urea or guanidinium hydrochloride). The protein gets denatured by this treatment. To attain a correctly folded protein, the denaturing agent must then be removed. This can be accomplished, e.g., by dialysis, dilution or diafiltration. For some proteins, as is the case with trypsinogen, the process of refolding is greatly enhanced if the free cystein residues of the denatured protein are blocked by the formation of mixed disulfides with glutathione or by S-sulfonation. This is accomplished by the treatment of the denatured protein solution with oxidized glutathione or with $SO_3^{2-}$ and 2-nitro-5-(thiosulpho)-benzoate in the presence of a denaturing concentration of the chaotropic agent. After removal of the blocking solution, refolding is performed by removing the chaotropic agent, as described above.

The refolding procedure for trypsinogen is preferably performed by a new method which is also a part of the present invention. This method is not limited to the refolding of trypsinogen but is also applicable for refolding any denatured protein. It is a semi-continuous or continuous method and requires a reactor unit with the following minimal features (FIG. 1): a device for mixing, a connection to a diafiltration (or another equivalent filtration) circuit, an inlet for feeding the sample (i.e., the denatured protein), an inlet for feeding renaturation buffer, and an outlet for draining off product (i.e., renaturing and/or renatured protein).

The operation of this apparatus comprises the steps of feeding denatured protein to the reactor, removing denaturing agents via the diafiltration circuit and removing processed protein solution from the reactor. The reactor can be operated in a continuous or semi-continuous way. In the semi-continuos mode, feed into and volume removal from the reactor unit is done intermittently, e.g. in predetermined intervals depending upon the refolding properties of the treated protein. In continuous mode operation, the influxes and effluxes are adjusted to the refolding velocity of the concerned protein in order to maintain a desired dynamic steady state equilibrium within the reactor. While it is preferred that the flow rates are adjusted such as to allow for sufficient residence time of the denatured protein for substantially complete refolding (e.g. 95%) inside the reactor unit, it may be desired in some applications to adjust the flow rates such as to increase the throughput of the material while reducing the mean residence time of the protein inside the unit and to drain off protein whereof a substantial, optionally prevailing, portion is still in the process of refolding, thus allowing completion of refolding of that portion of denatured protein outside the reactor unit.

Apart from refolding denatured proteins, the apparatus can also be used for other treatments of protein solutions, e.g., for a continuous buffer exchange, or for blocking cystein residues, as described above.

The operation conditions for refolding are characterized as follows:

F1=Flux 1, feed denatured protein
F2=Flux 2, feed refolding buffer
F3=Flux 3, outlet diafiltrate
F4=Flux 4, outlet refolded protein By definition, F1 and F2 have positive values or 0 (zero), and F3 and F4 negative values or 0 (zero). Absolute values of F3 or F4 are indicated as |F3| or |F4|.

If constant volume and constant protein concentration in the reactor are desired, following conditions must be applied:

$$F1+F4=0 \quad (1)$$

and $$F2+F3=0 \quad (2)$$

For constant volume and increasing protein concentration:

$$F1+F2=|F3+F4|, \text{ with } F1>|F4| \text{ and } |F3|>F2 \quad (3)$$

For increasing volume and increasing protein concentration:

$$F1>|F4| \text{ and } (F1+F2)>|F3+F4|, \text{ e.g. } F2=|F3| \quad (4)$$

Generally, the concentration of denaturing agent will not be reduced to zero, but to an equilibrium level depending mainly on the flux levels. A certain low concentration of chaotropic agent is in most cases beneficial to the refolding rate. Based on the assumption of a constant volume and no retention of the denaturing agent at the diafiltration membrane (as is the case with, e.g., urea as denaturing agent), the following condition holds for an equilibrium state:

$$C_{F1} \times F1 + C_{F2} \times F2 + C_{F3} \times F3 + C_{F4} \times F4 = 0 \quad (5)$$

$C_{Fi}$ ... concentration of denaturing agent at flux i (i=1 to 4)

In an equilibrium state, $C_{F3}=C_{F4}=C_R$ (concentration in the reactor). If one assumes that F1=−F4 and $C_{F2}$=0, it follows that:

$$F3/F1=-(C_{F1}-C_R)/C_R \quad (6)$$

Following equation (6), the relation of F3 to F1 can be calculated based on the given value of $C_{F1}$ and the desired value of $C_R$.

Generally, F1 should be adjusted to the refolding rate of the protein. Therefore, depending on the respective refolding rate of a protein, values of F1 between 0.02 and 4 $h^{-1}$ are appropriate and preferred. Lower flow rates, though technically possible without negative effect to the refolding as such, are not preferred as they slow down the overall refolding process and thus reduce the process economy.

The main advantages of the refolding method according to the present invention comprise the following:
- the reactor size can be much smaller than with batch processes;
- for refolding in a batch system, the concentration of denatured protein (and of denaturing agent fed together with the denatured protein) must be kept sufficiently low (e.g., at a level of maximum 10-50 µg protein per ml renaturation buffer) to avoid protein aggregation, which requires providing a high starting volume of renaturing buffer in the batch system;
- the protein concentration can be substantially increased when the feeding rate of denatured protein is equal or lower than the refolding rate, while the removal of denaturing agent at least equals its introduction via the denatured protein feed;
- higher protein concentrations means smaller volumes for storage and reaction vessels and less consumption of chemicals (e.g. denaturing agents, buffer, cystein residue blocking agents);
- higher product yield is achievable than with batch processes;
- aseptic operation can easily be accomplished;
- considerable reduction of processing hence product costs.

In order that the invention described herein may be more fully understood, the following examples are set forth. The examples are for illustrative purposes and are not to be construed as limiting this invention in any respect. Particularly, it is understood that the procedures of the present invention, though mainly exemplified in the subsequent Examples for recombinant human trypsinogen 1 and its corresponding trypsin, are also applicable without inventive input to other human trypsinogens and the corresponding trypsins as well as to trypsinogens and corresponding trypsins of non-human origin, including bovine and porcine trypsinogens and trypsins. It is further understood that the present invention shall also comprise variations of the expressly disclosed embodiments to an extent as would be contemplated by a person of ordinary skill in the art.

EXAMPLE 1

Expression of Human Trypsinogen 1 in the Yeast *Pichia pastoris*

The gene for human trypsinogen 1 (Gene 41, 305-310, 1986; Swissprot locus TRY1_HUMAN, accession no. P07477; for the sequence see Table 1) was inserted into the vector pPICZαB (Invitrogen), which was previously digested with SfiI.

TABLE 1

Nucleotide sequence of the human trypsinogen 1 gene beginning at the propeptide sequence (SEQ ID NO 1)
GCCCCCTTTGATGATGATGACAAGATCGTTGGGGGCTACAACTGTGAGGA

GAATTCTGTCCCCTACCAGGTGTCCCTGAATTCTGGCTACCACTTCTGTG

GTGGCTCCCTCATCAACGAACAGTGGGTGGTATCAGCAGGCCACTGCTAC

AAGTCCCGCATCCAGGTGAGACTGGGAGAGCACAACATCGAAGTCCTGGA

GGGGAATGAGCAGTTCATCAATGCAGCCAAGATCATCCGCCACCCCCAAT

ACGACAGGAAGACTCTGAACAATGACATCATGTTAATCAAGCTCTCCTCA

CGTGCAGTAATCAACGCCCGCGTGTCCACCATCTCTCTGCCCACCGCCCC

TCCAGCCACTGGCACGAAGTGCCTCATCTCTGGCTGGGGCAACACTGCGA

GCTCTGGCGCCGACTACCCAGACGAGCTGCAGTGCCTGGATGCTCCTGTG

CTGAGCCAGGCTAAGTGTGAAGCCTCCTACCCTGGAAAGATTACCAGCAA

CATGTTCTGTGTGGGCTTCCTTGAGGGAGGCAAGGATTCATGTCAGGGTG

ATTCTGGTGGCCCTGTGGTCTGCAATGGACAGCTCCAAGGAGTTGTCTCC

TGGGGTGATGGCTGTGCCCAGAAGAACAAGCCTGGAGTCTACACCAAGGT

CTACAACTACGTGAAATGGATTAAGAACACCATAGCTGCCAATAGCTAA

TABLE 2

PCR primers for cloning into pPICZαB

Forward primer:
5' - CATGCCATGACTCGCGGCCCAGCCGGCCCCCTTTGATGATGATG - 3'   (SEQ ID NO 2)

Backward primer:
5' - CATGCCATGACTCGCGGCCGGCTGGGCCTTAGCTATTGGCAGCTATGG - 3'   (SEQ ID NO 3)

The corresponding SfiI sites were attached to the trypsinogen gene by PCR (primer sequences see Table 2). The recombinant plasmid was transformed into *P. pastoris* strain GS115 or strain X33, respectively, by electroporation. Positive yeast clones were selected by resistance to zeocin. Several clones were cultivated in 250 ml baffled shake flasks. As cultivation media, either buffered minimal medium (100 mM potassium phosphate, pH 6.0; 1.34% YNB; $4\times10^{-5}$% biotin; 1% glycerol or 0.5% methanol) or buffered complex medium (1% yeast extract; 2% peptone; 100 mM potassium phosphate, pH 6.0; 1.34% YNB; $4\times10^{-5}$% biotin; 1% glycerol or 0.5% methanol) was used. For induction of recombinant gene expression, the cells were centrifuged and resuspended in fresh medium containing methanol instead of glycerol. Then the cells were removed from the supernatant by centrifugation, and the recombinant trypsinogen was detected in the supernatant by SDS polyacrylamide gel electrophoresis. This procedure enabled the selection of strong overproducing clones. Activation of trypsinogen was not observed in these cultures.

Alternatively, the gene for human trypsinogen 1 (sequence see Table 1) was inserted into the vector pHILS1 (Invitrogen), which was previously digested with XhoI and BamHI. The corresponding XhoI and BamHI sites were attached to the trypsinogen gene by PCR (primer sequences see Table 3). The recombinant plasmid was transformed into *P. pastoris* strain GS115 by the protoplast transformation method. Positive yeast clones were selected by growth on minimal plates without histidin. Cultivation and analysis followed the procedures described above.

TABLE 3

PCR primers for cloning into pHILS1

Forward primer:                            (SEQ ID NO 4)
5' - CCGCTCGAGCCCCCTTTGATGATGATG - 3'

Backward primer:                           (SEQ ID NO 5)
5' - GCGGATCCTTAGCTATTGGCAGCTATGG - 3'

Both methods yielded secretion of correctly folded trypsinogen into the culture medium. Refolding was not necessary which rendered this yeast-based process for the manufacture of trypsinogen relatively simple and well suitable for industrial scale production, though optimization of the culturing conditions may be useful to further improve the product yield. The yield of secreted trypsinogen in the present experiments was lower than in the *E.coli* system (e.g., as a maximum only about 10% of the yield achieved with *E.coli*), and typically amounted to at least 10 mg/l in the shake flask culture at a biomass concentration of approximately 10 g/l (calculated as dry mass per liter of culture broth) and at least 30 mg/l in an agitated lab-scale fermenter vessel at a biomass concentration (calculated as dry mass) of approximately 30 g/l. As the present process still leaves room for optimization it is expected that a biomass concentration of up to 100 g/l (as reported in literature for various *P.pastoris* fermentation processes) and, correspondingly, a trypsinogen concentration of about 0.1 g/l in the culture supernatant may well be reached by changing some parameters of the nutrient medium and the culturing conditions alone.

Taking into account that in our experiments the culture supernatant contained only very few other proteins which considerably facilitates separation and purification (only one or two purification steps are required), and further that no denaturing or renaturing steps were necessary (because the secreted protein was already correctly folded) the final overall product yield obtainable by the yeast method was not so far from the one achieved by the *E.coli* method.

It is also emphasized that under the aforementioned expression and culturing conditions, secreted trypsinogen remained stable in the culture broth during several days of cultivation. No autocatalytic activation to trypsin was observed (probably due to the acidic pH of the cell culture suspension being in a range of from pH 2 to pH 7.5, which is far from being optimal for autocatalytic conversion of trypsinogen) nor any negative impact on cell viability. Thus, the avoidance of various undesired procedural developments including but not limited to uncontrolled trypsin formation, inhibition of cell growth, acceleration of cell lysis, trypsin autodigestion, supernatant pollution by cell components of lysed cells, additional purification steps, product contamination, product loss, etc. is believed to confer a considerable advantage of the present invention over the state-of-the-art technology.

EXAMPLE 2

Expression of Human Trypsinogen 1 in *Escherichia coli*

The expression vector pET3a (Studier et al. 1990) was digested either with NdeI and BamHI or with BamHI alone, and the human trypsinogen 1 gene was inserted. The corresponding restriction sites were attached by PCR (primer sequences see Table 4). The recombinant plasmid was transferred into *E. coli* K12 HMS174(DE3) by electroporation. Positive clones were selected by growth on ampicillin plates.

Unexpectedly, insertion of the gene for human trypsinogen 1 into the expression vector right after the start codon did not result in a measurable expression of the desired protein. Only after insertion of an oligonucleotide between the start codon and the trypsinogen gene high expression of trypsinogen was successfully achieved. Best results were obtained when using an oligonucleotide coding for several, preferably at least 10, amino acids, of a protein that is known to be highly expressed in a bacterial host, and particularly, when using a nucleotide sequence coding for the first 10 to 15 amino acids of the amino acid sequence of the phage T7 envelope protein.

TABLE 4

PCR primers for cloning into pET3a

SEQ ID NO 6
Forward primer (for cloning in the NdeI site):
5' - GGAATTCCATATGGCCCCCTTTGATGATGATG - 3'

SEQ ID NO 7
Forward primer (for cloning in the BamHI site):
5' - GCGGATCCGCCCCCTTTGATGATGATG - 3'

SEQ ID NO 8
Backward primer:
5' - GCGGATCCTTAGCTATTGGCAGCTATGG - 3'

Several clones were cultivated in baffled shake flasks in M9ZB medium (10 g/l bactotryptone; 5 g/l yeast extract; 5 g/l NaCl; 1 g/l $NH_4Cl$; 3 g/l $KH_2PO_4$; 6 g/l $Na_2HPO_4$; 4 g/l glucose; 0.25 g/l $MgSO_4 \cdot 7H_2O$). When the cultures reached an $OD_{600}=1$, 0.4 mg/ml IPTG was added for induction, and cultivation was continued for 4 hours. After cell lysis with lysozyme and Triton X-100 (0.4% in 10 mM TrisCl pH 8.2;

15 mM $MgCl_2$), recombinant trypsinogen was identified in the insoluble fraction of the lysates by western blotting.

Trypsinogen product yields (before denaturing and refolding) typically amounted to at least 20% by weight of bacterial biomass (calculated as dry mass) of the cell culture. Biomass yields of 20 g dry cell mass per 1 L of cell culture suspension could be achieved in agitated fermenter vessels, resulting in a product yield (trypsinogen) of 4 g/l. In spite of this remarkably high intracellular (i.e., cytoplasmic) accumulation of trypsinogen no negative impact thereof on the producing host cells was observed, which presumably is due to the biosynthesis and intracellular storage of the trypsinogen in the form of inactive aggregated proteins (inclusion bodies).

EXAMPLE 3

Refolding of Human Trypsinogen 1

After cell lysis (as described in Example 2), the insoluble fraction was centrifuged and washed two times in 3-4 M urea. Then the pellet was resuspended in denaturing solution (9 M urea; 100 mM TrisCl pH 8.6; 1 mM EDTA, 10 mM DTE) and incubated for 2.5 hours at 37° C. To remove DTE, the buffer of the supernatant was changed by ultrafiltration under nitrogen with washing buffer (8 M urea; 100 mM TrisCl pH 8.6; 1 mM EDTA). Then an equal volume of 200 mM oxidized glutathione in 8 M urea was added and the mixture incubated for 3 hours. Then the buffer was changed again with washing buffer.

For renaturation, a reactor unit as described hereinbefore was filled with refolding buffer (50 mM TrisCl pH 8.6; 50 mM $CaCl_2$ and a redox pair (e.g. cystein/cystin; reduced/oxidized glutathione), and refolding buffer was fed at a rate of 0.85 $h^{-1}$. At the same rate filtrate was withdrawn via the diafiltration circuit. Denatured protein was fed at a rate of 0.067 $h^{-1}$. The yield of refolded protein was at least 10% higher than that achieved with a comparable traditional batch procedure, and usually exceeded the 10% level considerably.

Activation of the purified trypsinogen to trypsin, regardless of the producing host cell system, may be carried out using any of the proteinases known in the art, such as bovine enteropeptidase or trypsins of various origin. It is, however, highly preferred according to the present invention to disregard all of these methods, which would contravene the concept of manufacture of a human recombinant trypsin, and to solely rely on the faint autocatalytic activity of the purified trypsinogen. Moreover, it was found that purely autocatalytic conversion (i.e., without the addition of any protease) of the purified human recombinant trypsinogen manufactured according to the present invention achieved the best product (i.e., active trypsin) yield, particularly when carried out by incubation at 30 to 37° C., preferably at a slightly alkaline pH between pH 7 and 8, for a period of several hours (e.g., 2-12 hours, depending on the starting amount of trypsinogen). Accordingly, in the preceding Examples 1 and 2 final conversion of trypsinogen to trypsin was carried out by autocatalysis only, i.e., without the addition of any trypsin or other proteinase. Additional information on parameters for autocatalytic conversion of trypsinogen to trypsin may be derived from, e.g., Kay, J. et al., J Biol Chem 246/21, 6661-6665, 1971).

EXAMPLE 4

Refolding of the Single Chain Antibody sc3D6

The feasibility of the refolding procedure was proven with another recombinant protein, a single-chain antibody (sc3D6). An *E. coli* clone expressing sc3D6 was cultivated as described in Example 2.

After cell lysis (according to Example 2), the insoluble fraction was centrifuged and washed two times in 3-4 M urea. Then the pellet was resuspended in denaturing solution (9 M urea; 100 mM TrisCl pH 8.6; 1 mM EDTA, 10 mM DTE) and incubated for 2.5 hours at 37° C. To remove DTE, the buffer of the supernatant was changed by ultrafiltration under nitrogen with washing buffer (8 M urea; 100 mM TrisCl pH 8.6; 1 mM EDTA). Then an equal volume of 200 mM oxidized glutathione in 8 M urea was added and the mixture incubated for 3 hours. Then the buffer was changed again with washing buffer.

For renaturation, a reactor unit (as described hereinbefore) was filled with refolding buffer (50 mM TrisCl pH 8.6; 50 mM $CaCl_2$ and a redox pair (e.g. cystein/cystin, or reduced/oxidized glutathione), and refolding buffer was fed at a rate of 3.0 $h^{-1}$. At the same rate filtrate was withdrawn from the diafiltration circuit. Denatured protein was fed at a rate of 0.1 $h^{-1}$. Again, a high yield of refolded protein was achieved.

EXAMPLE 5

Purification of Trypsinogen from Yeast Culture Supernatants

The culture supernatant was cooled and centrifuged. The cell pellet was discarded and the supernatant was centrifuged a second time. The pH of the supernatant was adjusted to 4.0 with acetic acid and 10 mM $CaCl_2$ was added. The supernatant was directly loaded onto a TosoHaas Toyopearl SP550C resin (strong cation exchanger), at a flow rate of 100 cm/h at either room temperature or 4° C., respectively. The column was washed with 50 mM NaAc/Hac+200 mM NaCl+10 mM $CaCl_2$. The protein is eluted with 50 mM NaAc/Hac+400 mM NaCl+10 mM $CaCl_2$. The recovery yield of trypsinogen, determined by the activity of trypsin, is about 87%.

EXAMPLE 6

Virus Treatment by Recombinantly Produced Human Trypsin 1

Recombinant human trypsin 1 prepared both from *E. coli* and from *P. pastoris* as described above was used for the treatment of influenza virus to induce the infectivity of the virus in cell culture. Different strains of influenza virus were compared in Vero/SF cells. The effect of recombinant human trypsin was compared to porcine trypsin, bovine trypsin and bovine chymotrypsin.

Procedure: after removal of the culture supernatant the cells were infected with 50 μl/well of virus dilution (1:1000; MOI appr. 0.01). After 20 min. incubation at room temperature, 500 μl/well of medium containing two-fold dilutions of different proteases were added. The trypsins of different origins were standardized to the same volumetric activity, measured with TAME (p-toluene-sulfonyl-L-arginine methyl ester) as the substrate. Typical trypsin concentrations were: 0.03-1 TAME units per ml of the final solution. One TAME unit is defined as the amount of trypsin hydrolyzing 1 μmol p-toluene-sulfonyl-L-arginine methyl ester per minute.

Recombinant human trypsin and porcine trypsin gave identical results and both were superior to bovine trypsin and chymotrypsin.

The invention claimed is:

1. A method for the manufacture of recombinant trypsinogen or trypsin comprising incubating transformed host cells expressing a trypsinogen gene in a suitable cell culture nutrient medium at conditions allowing for cell multiplication and simultaneous or subsequent expression of the trypsinogen gene, separating extracellularly accumulated trypsinogen from the cell suspension, characterized in that the method comprises incubating the transformed host cells at an acidic pH at or above pH 2, the transformed host cells being yeast cells transformed with an expression vector that contains a naturally occurring trypsinogen gene, and after incubation, during which no trypsinogen activation or trypsin activity is detected in the medium by SDS polyacrylamide gel electrophoresis, separating the cells from the medium, obtaining a solid-free supernatant containing correctly folded trypsinogen and subjecting said solid-free supernatant containing correctly folded trypsinogen to purification by chromatography without a preceding refolding or buffer exchanging step, and optionally further processing the separated trypsinogen.

2. A method according to claim 1, wherein the expression vector is selected from the group consisting of pPICZαB and pHILS1.

3. A method according to claim 2, wherein a trypsinogen gene containing a forward primer sequence according to SEQ ID NO 2 and a backward primer sequence according to SEQ ID NO 3 is inserted into the vector pPICZαB, or a trypsinogen gene containing a forward primer sequence according to SEQ ID NO 4 and a backward primer sequence according to SEQ ID NO 5 is inserted into the vector pHILS1.

4. A method according to claim 2, wherein the expression vector contains a secretion leader sequence for secretion of expressed trypsinogen.

5. A method according to claim 1, wherein the transformed host cells are incubated in the presence of methanol.

6. A method according to claim 1, wherein a protein-free medium is used as the nutrient medium.

7. A method according to claim 6, wherein the nutrient medium is a minimal medium comprising yeast nitrogen base YNB as the sole nitrogen source.

8. A method according to claim 1, wherein a $Ca^{2+}$ source is added to the supernatant before it is subjected to chromatography, to augment trypsinogen binding to a chromatography resin.

9. A method according to claim 8, wherein $Ca^{2+}$ is added at a concentration ranging from 0.5 to 500 mmol per liter.

10. A method according to claim 9, wherein $Ca^{2+}$ is added at a concentration ranging from 1 to 300 mmol per liter.

11. A method according to claim 9, $Ca^{2+}$ is added at a concentration ranging from 5 to 20 mmol per liter.

12. A method according to claim 1, wherein the yeast is selected from the group consisting of *Pichia, Saccharomyces, Hansenula* and *Kluyveromyces*.

13. A method according to claim 12, wherein the yeast is a *Pichia* species.

14. A method according to claim 12, wherein the yeast is *P. pastoris*.

15. A method according to claim 1, further comprising after subjecting the solid-free supernatant containing correctly folded trypsinogen to purification by chromatography a step of autocatalytically activating the purified trypsinogen to trypsin without an addition of trypsin or of any other proteinase.

16. A method according to claim 1, wherein the expression vector encodes bovine, porcine or human trypsinogen.

17. A method according to claim 16, wherein the expression vector encodes naturally occurring human trypsinogen 1.

18. A method according to claim 1, wherein the chromatography comprises the use of washing and/or eluting buffers and wherein $Ca^{2+}$ is contained in each washing and/or eluting buffer to facilitate subsequent activation of trypsinogen to trypsin.

19. A method according to claim 18, wherein $Ca^{2+}$ is contained in each washing and/or eluting buffer at a concentration of at least 0.5 mM.

20. A method according to claim 18, wherein $Ca^{2+}$ is contained in each washing and/or eluting buffer at a concentration of at least 1 mM.

21. The method of claim 1 utilizing a transformed yeast cell, wherein the yeast cell is transformed with an expression vector encoding naturally occurring human trypsinogen 1 having a nucleotide sequence according to SEQ ID NO.1, and wherein said expression vector is selected from the group consisting of pPICZαB in which the naturally occurring human trypsinogen 1 gene amplified with a forward primer having a sequence according to SEQ ID NO 2 and a backward primer having a sequence according to SEQ ID NO 3 is inserted; and pHILS1 in which the naturally occurring human trypsinogen 1 gene amplified with a forward primer having a sequence according to SEQ ID NO 4 and a backward primer having a sequence according to SEQ ID NO 5 is inserted, and wherein the transformed yeast cell secretes correctly folded human trypsinogen 1 when incubated.

22. A method according to claim 1, wherein the purification by chromatography without a preceding refolding or buffer exchanging step comprises purification by cation exchange chromatography.

* * * * *

SEQUENCE LISTING

```
<160> NUMBER OF SEQ ID NOS: 8

<210> SEQ ID NO 1
<211> LENGTH: 699
<212> TYPE: DNA
<213> ORGANISM: Homo sapiens

<400> SEQUENCE: 1
gccccctttg atgatgatga caagatcgtt gggggctaca actgtgagga gaattctgtc      60
ccctaccagg tgtccctgaa ttctggctac cacttctgtg gtggctccct catcaacgaa     120
cagtgggtgg tatcagcagg ccactgctac aagtcccgca tccaggtgag actgggagag     180
cacaacatcg aagtcctgga ggggaatgag cagttcatca atgcagccaa gatcatccgc     240
cacccccaat acgacaggaa gactctgaac aatgacatca tgttaatcaa gctctcctca     300
cgtgcagtaa tcaacgcccg cgtgtccacc atctctctgc ccaccgcccc tccagccact     360
ggcacgaagt gcctcatctc tggctggggc aacactgcga gctctggcgc cgactaccca     420
gacgagctgc agtgcctgga tgctcctgtg ctgagccagg ctaagtgtga agcctcctac     480
cctggaaaga ttaccagcaa catgttctgt gtgggcttcc ttgagggagg caaggattca     540
tgtcagggtg attctggtgg ccctgtggtc tgcaatggac agctccaagg agttgtctcc     600
```

```
tggggtgatg gctgtgccca gaagaacaag cctggagtct acaccaaggt ctacaactac      660
gtgaaatgga ttaagaacac catagctgcc aatagctaa                             699
```

<210> SEQ ID NO 2
<211> LENGTH: 44
<212> TYPE: DNA
<213> ORGANISM: Artificial Sequence
<220> FEATURE:
<223> OTHER INFORMATION: PCR Primer

<400> SEQUENCE: 2

```
catgccatga ctcgcggccc agccggcccc ctttgatgat gatg                        44
```

<210> SEQ ID NO 3
<211> LENGTH: 48
<212> TYPE: DNA
<213> ORGANISM: Artificial Sequence
<220> FEATURE:
<223> OTHER INFORMATION: PCR Primer

<400> SEQUENCE: 3

```
catgccatga ctcgcggccg gctgggcctt agctattggc agctatgg                    48
```

<210> SEQ ID NO 4
<211> LENGTH: 27
<212> TYPE: DNA
<213> ORGANISM: Artificial Sequence
<220> FEATURE:
<223> OTHER INFORMATION: PCR Primer

<400> SEQUENCE: 4

```
ccgctcgagc ccctttgat gatgatg                                            27
```

<210> SEQ ID NO 5
<211> LENGTH: 28
<212> TYPE: DNA
<213> ORGANISM: Artificial Sequence
<220> FEATURE:
<223> OTHER INFORMATION: PCR Primer

<400> SEQUENCE: 5

```
gcggatcctt agctattggc agctatgg                                          28
```

<210> SEQ ID NO 6
<211> LENGTH: 32
<212> TYPE: DNA
<213> ORGANISM: Artificial Sequence
<220> FEATURE:
<223> OTHER INFORMATION: PCR Primer

<400> SEQUENCE: 6

```
ggaattccat atggcccccct ttgatgatga tg                                    32
```

<210> SEQ ID NO 7
<211> LENGTH: 27
<212> TYPE: DNA
<213> ORGANISM: Artificial Sequence
<220> FEATURE:
<223> OTHER INFORMATION: PCR Primer

<400> SEQUENCE: 7

```
gcggatccgc ccctttgat gatgatg                                            27
```

<210> SEQ ID NO 8
<211> LENGTH: 28

```
<212> TYPE: DNA
<213> ORGANISM: Artificial Sequence
<220> FEATURE:
<223> OTHER INFORMATION: PCR Primer

<400> SEQUENCE: 8
gcggatcctt agctattggc agctatgg                                28
```